United States Patent
Bertrand

(10) Patent No.: US 6,311,544 B1
(45) Date of Patent: Nov. 6, 2001

(54) SELECTIVE REMOVAL OF VOLATILE SUBSTANCES INJECTED INTO A CHROMATOGRAPHIC PACKING FILLED COLUMN

(75) Inventor: Michel Bertrand, Verdun (CA)

(73) Assignee: Universite de Montreal, Montreal (CA)

( * ) Notice: Subject to any disclaimer, the term of this patent is extended or adjusted under 35 U.S.C. 154(b) by 0 days.

(21) Appl. No.: 09/638,849

(22) Filed: Aug. 16, 2000

Related U.S. Application Data

(62) Division of application No. 08/730,395, filed on Oct. 15, 1996, now Pat. No. 5,929,321, which is a continuation of application No. 09/181,860, filed on Oct. 29, 1998, now Pat. No. 6,131,440.

(51) Int. Cl.[7] .......................... B01D 15/08; B01D 13/08; G01N 30/08; G01N 30/30
(52) U.S. Cl. .................. 73/23.35; 73/23.39; 73/61.55; 95/86; 96/103; 210/198.2; 422/89
(58) Field of Search ................... 73/23.35, 23.39, 73/61.55; 95/87, 86, 12, 22; 96/103, 104, 105; 422/89; 210/198.2, 656, 659

(56) References Cited

U.S. PATENT DOCUMENTS

| | | | |
|---|---|---|---|
| 3,023,835 | 3/1962 | Brashear | 183/2 |
| 3,035,383 | 5/1962 | Sanford et al. | 55/67 |
| 3,043,127 | * 7/1962 | DeFord | 73/23 |

(List continued on next page.)

FOREIGN PATENT DOCUMENTS

| | | |
|---|---|---|
| 0051778 | 5/1982 | (EP) . |
| 1155687 | 6/1969 | (GB) . |
| 0498549 | 5/1976 | (SU) . |
| WO 93/17771 | 9/1993 | (WO) . |

OTHER PUBLICATIONS

Journal of Analytical Chemistry of the USSR, vol. 30, No. 1, Jan. 1975—A Translation of Zhurnal Analiticheskoi Khimili, pp. 328–329, I.A. Silaeva et al, "Determination of the Mixtures of Components by Overload Chromatography".

Analytical Chemistry, vol. 61, No. 14, Jul. 15, 1989, pp. 1478–1485, XP 000101956, Fuggerth E., "Zone Gas Chromatography".

Primary Examiner—Hezron Williams
Assistant Examiner—David J. Wiggins
(74) Attorney, Agent, or Firm—Swabey Ogilvy Renault Anglehart, James

(57) ABSTRACT

A flow of a carrier gas through a column is provided. A sample is provided in the column, and a temperature of a longitudinally short portion of the column is raised to a predetermined controlled high temperature at which volatile substances are released from the sample packing and are carried by the carrier gas. The column is cooled on each side of the short portion to a low temperature at which the volatile substances condense or adsorb on the column packing. By continuously moving the heated short portion from an inlet end to an outlet end of the packing in a direction of carrier gas flow the volatile substances selected by the controlled high temperature are released. Four particularly useful and advantageous applications can be identified for the invention. Firstly, it provides an improved gas chromatograph (GC) injector. Secondly, it provides an improved thermal separator or extractor. Thirdly, it provides an efficient way to analyze target compounds suspected of being contained within a complex mixture by allowing for the GC analysis to be carried out only on those compounds or substances falling within the same or similar thermal desorption characteristics as those of the target compound. Lastly, by operating in a full time-coupled time-resolved (TCRC) mode, a complete three-dimensional analysis output can be obtained giving better power of separation of the analyzed sample, which is of particular importance when the substance to be analyzed is a complex organic material.

8 Claims, 16 Drawing Sheets

U.S. PATENT DOCUMENTS

| | | | |
|---|---|---|---|
| 3,043,128 | 7/1962 | Ayers | 73/23 |
| 3,062,038 | 11/1962 | Ayers | 73/23 |
| 3,111,023 | 11/1963 | Overfield | 73/23 |
| 3,146,616 * | 9/1964 | Loyd | 73/23.1 |
| 3,159,019 | 12/1964 | De Ford | 73/23 |
| 3,225,521 | 12/1965 | Burow | 55/67 |
| 3,503,183 | 3/1970 | Kaiser | 55/67 |
| 3,578,757 | 5/1971 | Samuilov et al. | 73/23.1 |
| 3,581,465 * | 6/1971 | Haruki et al. | 55/67 |
| 4,042,350 | 8/1977 | Phillips | 55/28 |
| 4,353,243 | 10/1982 | Martin | 73/23.1 |
| 4,472,631 | 9/1984 | Enke et al. | 250/281 |
| 4,476,713 | 10/1984 | Alfredson | 73/61.1 C |
| 4,479,380 * | 10/1984 | Novotny | 73/61.1 C |
| 4,879,247 | 11/1989 | Ohlson | 436/527 |
| 4,883,504 | 11/1989 | Gerstel | 55/67 |
| 4,923,486 | 5/1990 | Rubey | 55/67 |
| 4,935,145 | 6/1990 | Cortes et al. | 210/656 |
| 5,028,243 | 7/1991 | Rubey | 55/67 |
| 5,108,466 | 4/1992 | Klein et al. | 55/20 |
| 5,108,468 | 4/1992 | Ligon, Jr. | 55/67 |
| 5,121,493 | 6/1992 | Ferguson | 395/600 |
| 5,135,549 | 8/1992 | Phillips et al. | 55/67 |
| 5,141,532 | 8/1992 | Sacks et al. | 55/67 |
| 5,152,176 * | 10/1992 | Bryselbout et al. | 73/23.41 |
| 5,168,746 * | 12/1992 | Madhusudhan et al. | 73/23.35 |
| 5,193,681 | 3/1993 | Lievsay | 206/444 |
| 5,196,039 | 3/1993 | Phillips et al. | 55/67 |
| 5,205,987 | 4/1993 | Ashraf-Khorassani et al. | 422/83 |
| 5,215,556 * | 6/1993 | Hiller et al. | 55/67 |
| 5,236,593 | 8/1993 | Cortes et al. | 210/656 |
| 5,238,557 * | 8/1993 | Schneider et al. | 210/198.2 |
| 5,288,310 | 2/1994 | Peters et al. | 96/104 |
| 5,372,716 | 12/1994 | Levy et al. | 210/198.2 |
| 5,376,277 | 12/1994 | Cortes et al. | 210/659 |
| 5,403,386 | 4/1995 | Collier et al. | 96/105 |
| 5,492,555 * | 2/1996 | Strunk et al. | 95/86 |
| 5,611,846 * | 3/1997 | Overton et al. | 96/102 |
| 5,808,178 * | 9/1998 | Roundbehler et al. | 73/23.39 |

\* cited by examiner

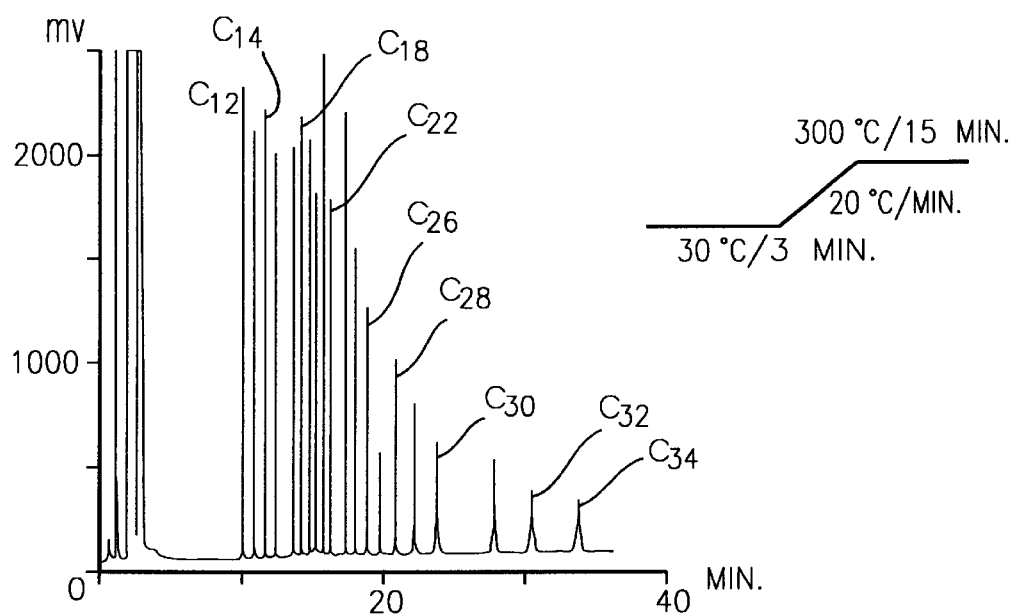
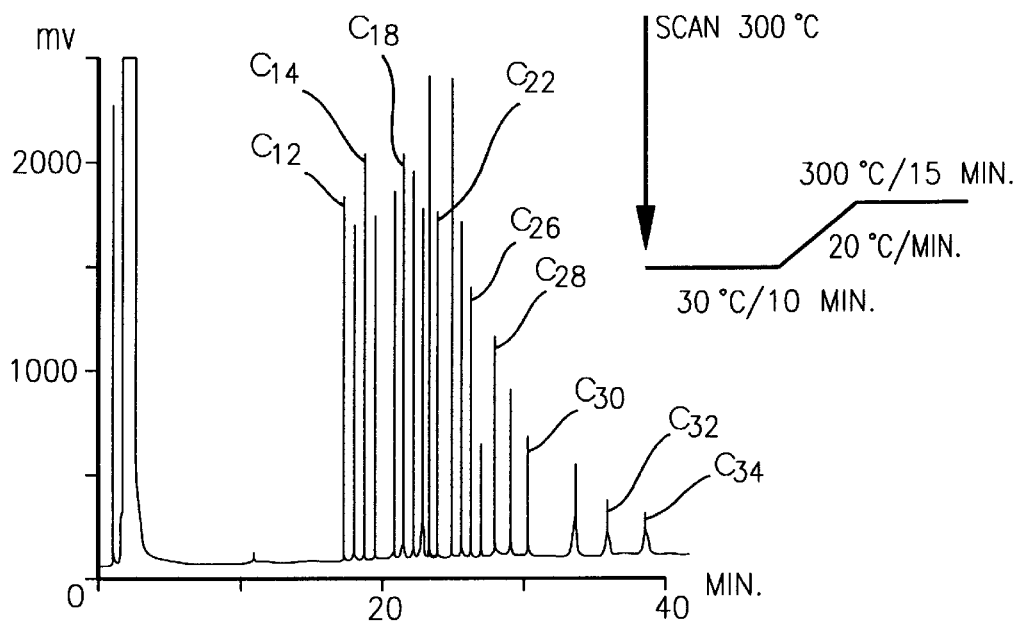
Figure 7 : OPERATION OF THE TCRC INSTRUMENT IN ITS GC EMULATION MODE. THE TOP CHROMATOGRAM WAS OBTAINED ON A CONVENTIONAL GAS CHROMATOGRAPH AND THE BOTTOM CHROMATOGRAM ON THE TCRC INSTRUMENT IN THE GC EMULATION MODE.

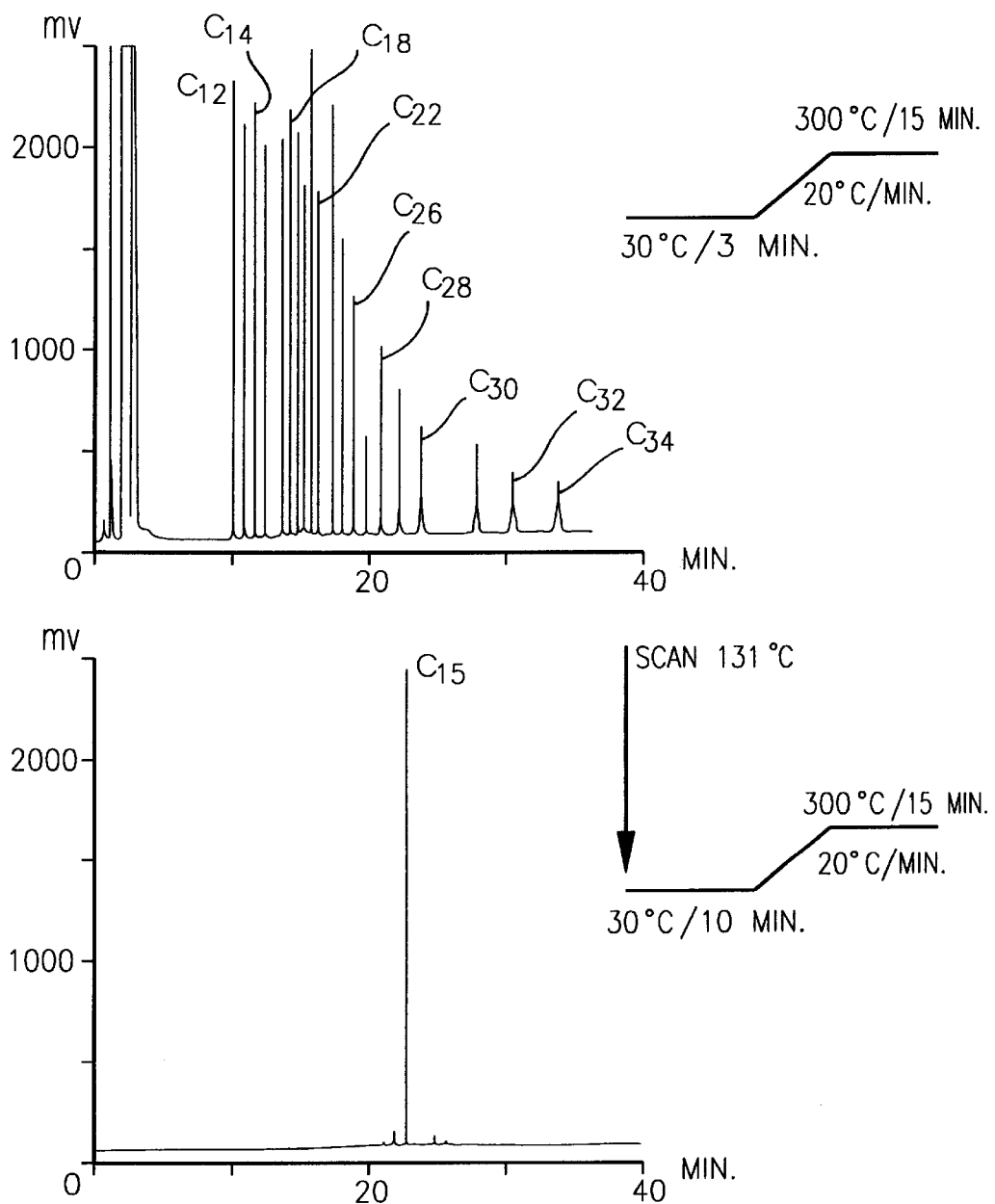
Figure 8 : OPERATION OF THE TCRC INSTRUMENT IN ITS TARGET COMPOUND ANALYSIS MODE MODE. THE TOP CHROMATOGRAM WAS OBTAINED ON A CONVENTIONAL GAS CHROMATOGRAPH AND THE BOTTOM CHROMATOGRAM ON THE TCRC INSTRUMENT IN ITS TARGET COMPOUND ANALYSIS MODE.

SELECTIVE REMOVAL OF VOLATILE SUBSTANCES INJECTED INTO A CHROMATOGRAPHIC PACKING FILLED COLUMN

This application is a divisional of U.S. patent application Ser. No. 08/730,395, filed Oct. 15, 1996, now U.S. Pat. No. 5,929,321, and a continuation of U.S. patent application Ser. No. 09/181,860, filed Oct. 29, 1998, now U.S. Pat. No. 6,131,440 granted on Oct. 17, 2000.

TECHNICAL FIELD

The present invention provides improved separation of chemical substances using chromathermographic techniques. When used in conjunction with a gas chromatograph, the invention further provides time-coupled time-resolved chromatography in which analysis of complex organic chemical mixtures is improved by providing a first separation according to thermal desorption characteristics followed by simplified gas chromatography. The invention has application in the areas of environmental analysis, biomedical analysis, drug screening and metabolism, biotechnologies, fuel analysis and many other areas in which it is necessary to characterize chemical species which are found in complex mixtures.

BACKGROUND OF THE INVENTION

In chromatography, a mixture, vaporized in a carrier gas, is introduced into a column where differential migration of the compounds, through the column, results in their separation. The compounds take different times to travel the length of the column. Compounds having more affinity for the packing in the column will tend to be retained in the packing, and their migration through the column will take a longer time. However, as the number of compounds in the mixture increases, it becomes likely that two or ore compounds will have similar affinities for the packing and, therefore, their migration times will become close to one another or almost identical. When this occurs, the compounds to not separate, and they will co-elute from the column. One of the ways that can be used to separate the co-eluted chemicals is re-injecting the non-separated compounds into a second chromatographic column as they elute from the first. In this "heart-cutting" technique, the flow of the first column is diverted into a second column temporarily at the elution time of the non-separated components. The chromatographic process continues on the second column which has a different packing, and separation can be achieved, as shown in FIG. 1. In this technique that uses two gas chromatographs combined in series, the mixture has to be re-injected if another "heart-cut" is to be made in order to separate another region of the chromatogram.

A second approach that has been proposed produces multidimensional separation by modulating the temperature of the chromatographic column. In this arrangement, the sample flows through a first column at a given temperature, and the column is continuously modulated in temperature at its end. The temperature is cooled so as to temporarily retain compounds in the flow for a short period of time, and then flash-heated in order to desorb them into a second column in series with the first. Thus, at periodic times, the second column analyzes compounds that have been trapped at the end of the first and acts as a second dimension. The arrangement is shown in FIG. 2. It is limited in the number of compounds that it can ultimately separate because the analysis cycle is short in the second dimension (=2 seconds).

Furthermore, the technique has only one mode of operation and cannot be used for the selective and rapid analysis of one or several target compounds present in a mixture. Thus it seems to be better than conventional chromatography and superior to heart-cutting, since it can expand many regions of a chromatogram using a single injection of the sample.

In the field of gas chromatography injectors, it is desirable to inject in the gas phase the substances to be analyzed by the gas chromatograph as a "short square pulse". The start time of passage through the gas chromatographic separation column should be substantially the same for all of the injected sample to be analyzed. When injecting high volumes of sample, conventional injectors have difficulty releasing the substances to be analyzed in an efficient square pulse manner. Furthermore, many complex organic compounds (normally in a solid phase at room temperature) are preferably injected in solution, only for the solvent to be discharged at the temperature of the analysis and for the remaining compounds to be released in gas form at the high temperature of analysis. This known method of injection is limited by the amount of solution which can be injected, due to the possible harmful effect on the gas chromatograph performance caused by a large amount of solvent being discharged in order to release a satisfactory amount of compounds from the solution. Furthermore, the chromatographic column can be saturated or blocked if too high amounts of compound are injected.

It is an object of the present invention to provide an apparatus for superior qualitative analysis of complex chemical mixtures.

It is a further object of the present invention to provide an apparatus and method for the separation and identification of complex chemical mixtures.

In "Zone Gas Chromatography" by Endre Fuggerth, *Analytical Chemistry*, Vol. 61, No. 14, Jul. 15, 1989, pp. 1478–1485, there is described an apparatus for selectively removing volatile substances injected into a packing filled column. The disclosed device has a narrow furnace passing over a column in which a substance to be analyzed is injected. As the furnace is passed over the zone containing the packing, substances thermally desorbed are released and carried by a carrier gas passing through the column. When the furnace surpasses the packing zone, the substances released go into a gas chromatography oven. The ability of the disclosed device to efficiently release substances into the gas chromatography (GC) apparatus is limited. Rapid release of the volatile substances from the packing filled column into the GC within a short period of time is lost due to the width of the heated zone or area by the narrow furnace.

It is an object of the present invention to provide an apparatus for superior qualitative analysis of complex chemical mixtures.

It is a further object of the present invention to provide an apparatus and method for the separation and identification of complex chemical mixtures.

It is yet another object of the present invention to provide an apparatus for selectively removing volatile substances injected into a packing filled column in which a very short portion of the column is raised to a desired high temperature and swept over the packing to release volatile substances.

SUMMARY OF THE INVENTION

According to the invention, there is provided an apparatus for selectively removing volatile substances injected into a packing filled column, comprising: a carrier gas inlet provided at one end of the column; a carrier gas outlet provided at an opposite end of the column; mobile heating means able to controllably raise a temperature of a longitudinally short portion of the column for the volatile substances to be released from the packing and be carried by the carrier gas toward the outlet; cooling means for cooling the column on each side of the short portion to a low temperature at which the volatile substances condense on the packing; and control means for setting a temperature of the heating means and for causing the heating means to move over the packing in a direction of carrier gas flow to release the volatile substances selected by the temperature of the heating means.

It has been found that the provision of cooling means such as a water cooled disc or jets of cooling gas provided to cool the column on each side of the short portion raised by the heating means to the desired high temperature is effective in improving efficiency of the apparatus both for the purposes of providing an improved GC injector and for providing a chemical substance extractor for separating substances from a complex mixture of substances according to thermal desorption characteristics. In the case of an injector, the invention provides a relatively large column for containing and storing the substances to be analyzed. Selective and sudden release of the substances in a narrow square pulse is made possible by the heating and cooling means. In the case that the substances to be analyzed are contained in solution, the most volatile solvent can be initially released and vented without passing into the GC, thus increasing the efficiency of the analysis. The injection can be repeated while venting the solvent which allows the injection volume to be increased. Selective release of some of the compounds using the heating means into the GC avoids the saturation of the GC column. In the case that the substances to be analyzed are in solid, permeable form, it may be possible to insert the solid sample into the column for direct removal of the substances to be analyzed by the GC.

When the apparatus according to the invention is coupled to a GC, the invention further provides an apparatus for carrying out time-coupled time-resolved chromatography (TCRC) in which a sample of the substance to be analyzed is injected into the packing filled column and then the GC analysis is carried out in a plurality of stages related to a plurality of temperatures at which the mobile heating means are operated to release a portion of the sample, the entirety of the sample being released as the temperature of the heating means is increased to its maximum final temperature. The result is that each GC analysis is limited to a fewer number of substances, and therefore, is simplified. By arranging the GC results according to the heating means temperature, the chemical analysis data is given a three-dimensional perspective. In accordance with this aspect of the invention, the control means according to the invention comprise means for setting an initial and a final temperature for the heating means temperature; means for determining a temperature increment; cycling means for causing the heating means to repeatedly remove the substances from the packing for release into the gas chromatograph beginning at the initial temperature and ending at the final temperature by the temperature increment; delay means for delaying the cycling means to space apart the consecutive release of the substances by an amount of time required to prevent overlap of analysis; and means for recording results of the analysis by the gas chromatograph for each cycle along with the heating means temperature for each cycle.

According to the invention, there is also provided a method for selectively removing volatile substances injected into a packing filled column, comprising the steps of:

a) providing a flow of a carrier gas through the column;
b) raising a temperature of a longitudinally short portion of the column to a predetermined controlled high temperature at which the volatile substances are released from the packing and be carried by the carrier gas;
c) cooling the column on each side of the short portion to a low temperature at which the volatile substances condense or adsorb on the packing; and
d) continuously moving the heated short portion from an inlet end to an outlet end of the packing in a direction of carrier gas flow to release the volatile substances selected by the controlled high temperature.

Preferably, at least one incomplete pass using the mobile heating means is carried out, i.e. the short portion of the column raised to the predetermined controlled high temperature is moved from the upstream end of the packing to a point near the downstream end of the packing so as to leave the volatile substances released at the controlled high temperature deposited near the downstream end of the packing. After completing the at least one incomplete pass, a complete pass is carried out during which the volatile substances are released as a result of the heated short portion passing over the downstream end of the packing. In this way, a higher portion of the volatile substances which can be released at the predetermined controlled high temperature are released into the outgoing flow of carrier gas.

Four particularly useful and advantageous applications can be identified for the apparatus and method according to the present invention. Firstly, the invention can be used to provide an improved GC injector. Secondly, the invention can be used to provide an improved thermal separator or extractor. Thirdly, the invention provides an efficient way to analyze target compounds (Target Compound Analysis or TCA mode) suspected of being contained within a complex mixture by allowing for the GC analysis to be carried out only on those compounds or substances falling within the same or similar thermal desorption characteristics as those of the target compound. Lastly, by operating in a full TCRC mode, a complete three-dimensional analysis output can be obtained giving better power of separation of the analyzed sample, which is of particular importance when the substance to be analyzed is a complex organic material. The latter mode produces a novel type of mapping of analytical results that indicates the true complexity of the sample. As can be appreciated, the apparatus according to the invention preferably comprises a vent at the outlet of the column whereby a scan by the heating means releasing substances which are of little analytical interest can be discarded before carrying out a subsequent scan at a higher temperature to release substances of interest which, instead of being vented, are injected into the GC or are collected or otherwise trapped for subsequent use.

As can also be appreciated, the invention has application in those cases where conventional GC fails to resolve between two closely related peaks by providing an accurate way to carry out a plurality of GC analyses with the sample separated according to thermal desorption characteristic. As can be appreciated, the invention allows the separation of more components per analysis (five to ten times) than conventional GC.

When the substance detector provided at the output of the GC is a mass spectrometer, a more accurate and positive identification of the substance making up each peak in the GC result is provided. The invention allows by the use of pattern recognition to merge signals caused by a single compound eluding in several thermal scans.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 7 is a graphic representation of the TCRC device in its gas chromatograph emulation mode;

FIG. 8 is a graphic representation of the TCRC in the target analysis mode;

DETAILED DESCRIPTION OF THE PREFERRED EMBODIMENTS

Figure 11:
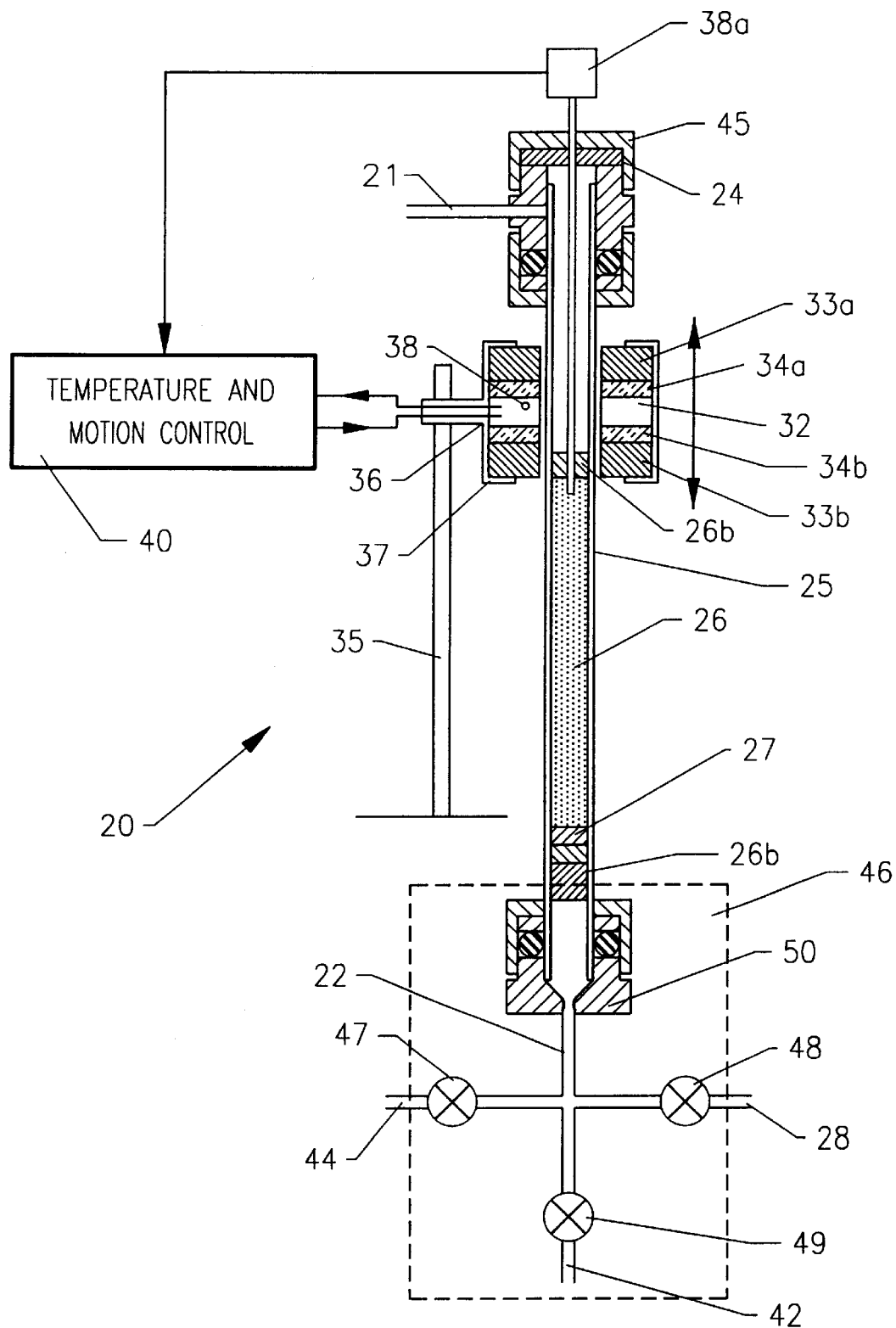
FIG. 11 is a cross-sectional elevation view of the injector column according to the invention.

As mentioned above, the present invention has at least four separate applications. The basic apparatus 20 comprises, as illustrated in FIG. 11, a column 25 filed with a stationary phase or packing 26 and glass wool end plugs 26b. A carrier gas inlet 21 provides a source for carrier gas flow through the column 25. The outlet 22 is illustrated as communicating with a gas chromatograph inlet 42, a vent or trap 28 and a second carrier gas inlet 44. In the case of a solution to be analyzed or separated, a needle injector is inserted through septum 24. A septum cap 45 is provided. The mobile heating unit 30 comprises an electric ring heater 32 mounted on a positioning motor unit 36. Water cooled rings 33a and 33b are mounted with the heater 32 by a bracket 37, and insulation 34a and 34b is provided between the heater 32 and the rings 33. The gap between the glass, fused silica or quartz column 25 and the heater 32 and cooling rings 33 is less than 50 µm, and preferably the tolerance of the diameter of the column is good enough to allow for a very small gap. As illustrated schematically, the motor mounting 36 moves on a rack support 35. Motor movement and control of the temperature is carried out by control circuit 40. A temperature sensor 38 generates a temperature reference signal used for temperature control.

A sensor probe 38a is also inserted into the column at the top and extends into the top of the packing 26. This probe 38a is used to calibrated the internal temperature of the column as a function of scanning speed. Unit 30 is passed over sensor 38a whenever its speed or temperature has to be changed. A feedback circuit contained within circuit 40 ensures that the power input into the heating element 32 is sufficient to obtain the desired temperature at the given scan speed.

When a solution or liquid is injected into column 25 through the septum 24, adsorption in packing 26 takes place. Such adsorption may take place over a relatively large volume. As the heated zone sweeps over the packing 26, volatile substances are thermally desorbed and carried by the carrier gas towards the outlet 22. As illustrated at 27, a concentrated band of substances released at the temperature of the packing raised by the heater 32 is can be created by sweeping the mobile heater unit 30 to almost the end of the packing. After completing such an incomplete sweep, a complete sweep can be carried out and the substances can be released into the outlet 22.

As can be seen, in the embodiment illustrated in FIG. 11, a temperature controlled transfer zone 46 is present. The end of column 25 is seated in a column end fitting 50 communicating with outlet tube 22. A second carrier gas inlet 44 is connected via a valve 47 to outlet 22. A purge valve 48 is also connected to outlet 22 and leads to a vent or cold trap conduit 28. Also connected to outlet 22 is a valve 49 controlling flow from the outlet into a gas chromatograph inlet 42.

Figure 12:
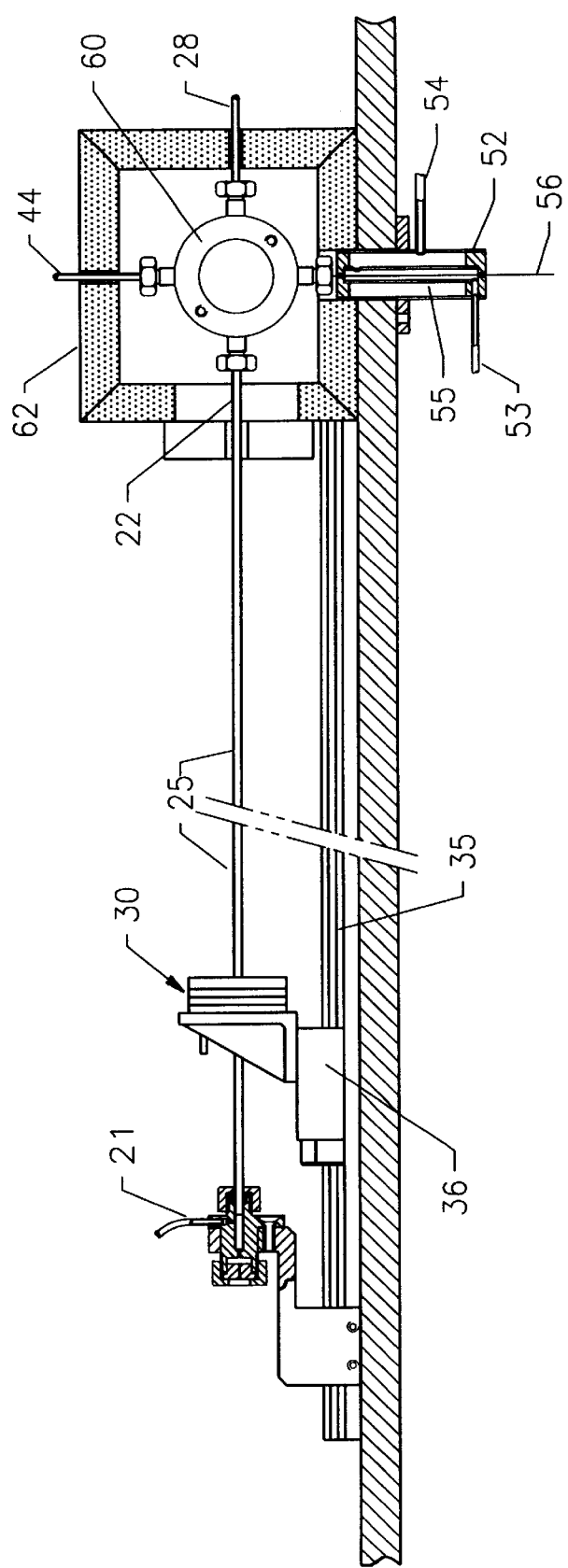
FIGS. 12 and 13 are a side and top view respectively of an injector column, four-way valve and cold trap assembly according to the invention.
Figure 13:
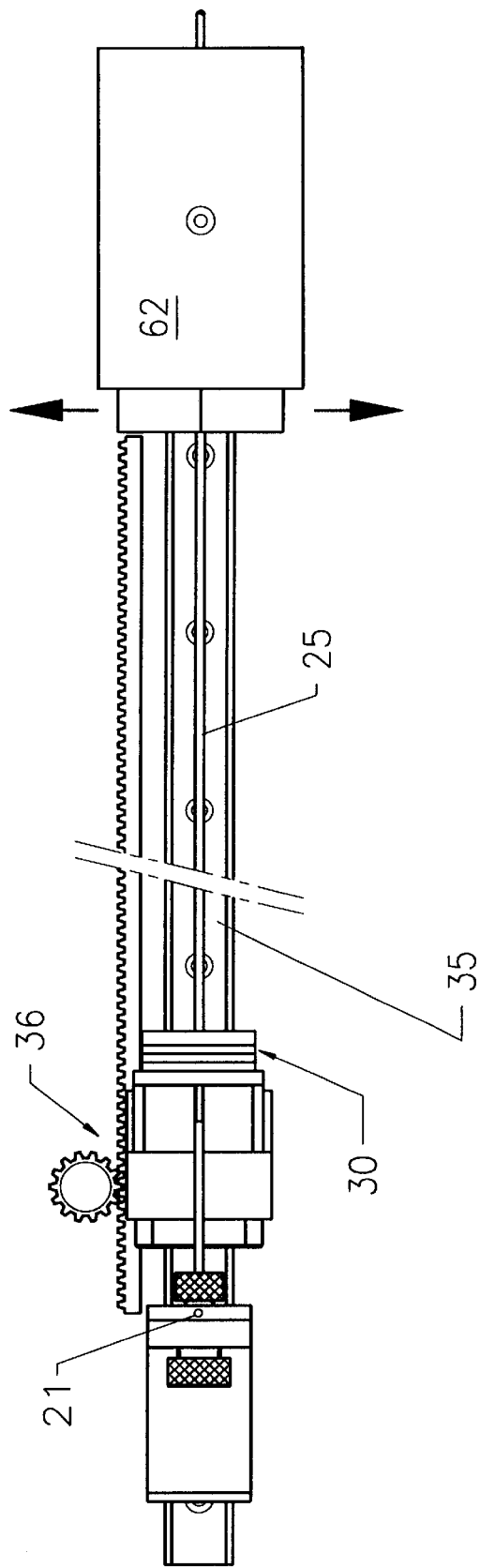
Figure 14:
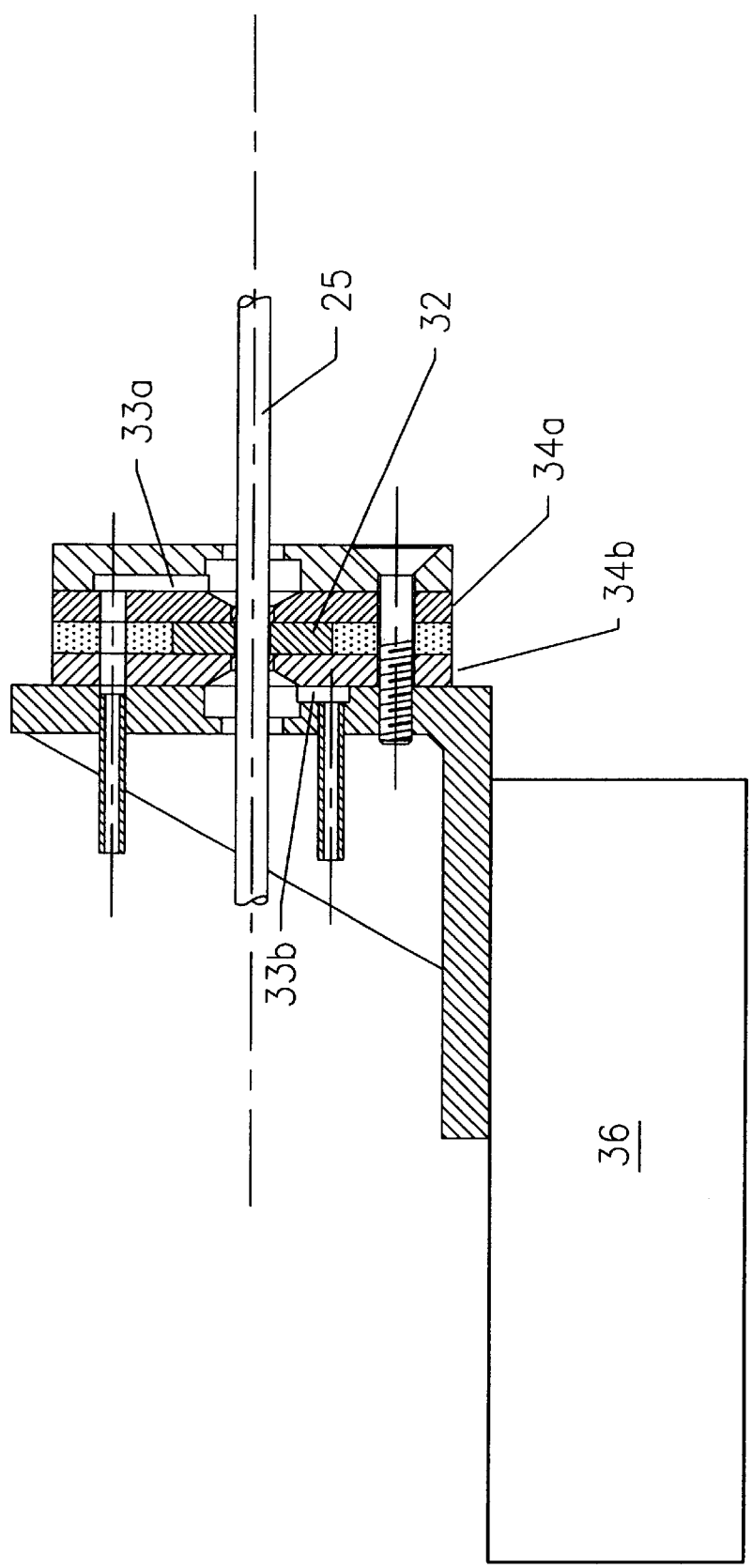
FIG. 14 is sectional view of the heating means and cooling means of the embodiment of FIGS. 12 and 13.

As illustrated in FIGS. 12 through 14, a different embodiment of the invention contemplates a horizontal arrangement in which the column 25 leads into a four-way valve 60 for connecting the carrier gas flow from column 25 to either a cold trap 62 or a vent 28. As seen in FIG. 13, a driven pinion gear and rack assembly are used to drive the mobile heating means 30 along the length of column 25. As seen in FIG. 14, this embodiment contemplates the use of air or $CO_2$ for cooling the zones on each side of the heater element 32 is by forced convection. As illustrated in FIG. 12, the four-way valve 60 is contained within a heated chamber 62 to keep the valve and fittings at a temperature at which adsorption of the removed substances is prevented. The cold trap 62 comprises a cold gas inlet 53 and a cold gas outlet 54, the cold gas inlet 53 communicating with a heater tube 55 at its lower end. The heater tube 55 has an opening in its upper end for communicating the cooling gas with the surrounding chamber and the cooling gas outlet 54. The released substances passing into the heater tube 55 from the four-way valve 60 are adsorbed onto the surface of the heater tube 55. Release of the adsorbed materials is achieved by heating electrically tube 55 and allowing the carrier gas flow to transport the substance into the upper end of the gas chromatography capillary column 56.

In the embodiment illustrated in FIGS. 12 and 13, the column is approximately 50 centimeters long (range of about 10 cm to 150 cm) to permit accurate separation of the materials adsorbed in column 25. This embodiment is particularly useful for TCRC and TCA analyses. In the embodiment of FIG. 11, an injector may be provided in which case the column height may be as short as a few centimeters.

As can be appreciated, the heating device 32 could also comprise a radiative element or even a laser source. The motor positioning device 36 could also in the case of a laser be replaced by suitable optics to move the point of radiative energy along the column. The column could also comprise a radiation absorbing lining to absorb the radiation and prevent penetration of the radiation to the inside the column. It would also be possible to direct a plurality of cooling gas jets along the entire length of the column. In the case that radiative means are used to heat the longitudinally short portion of the column, it is also possible to provide a cooling jacket on a column through which a cooling fluid would be circulated provided that the jacket and fluid are substantially transparent to the heating radiation.

The preferred embodiment of the invention in which a TCRC device is provided is now described.

Figure 1:
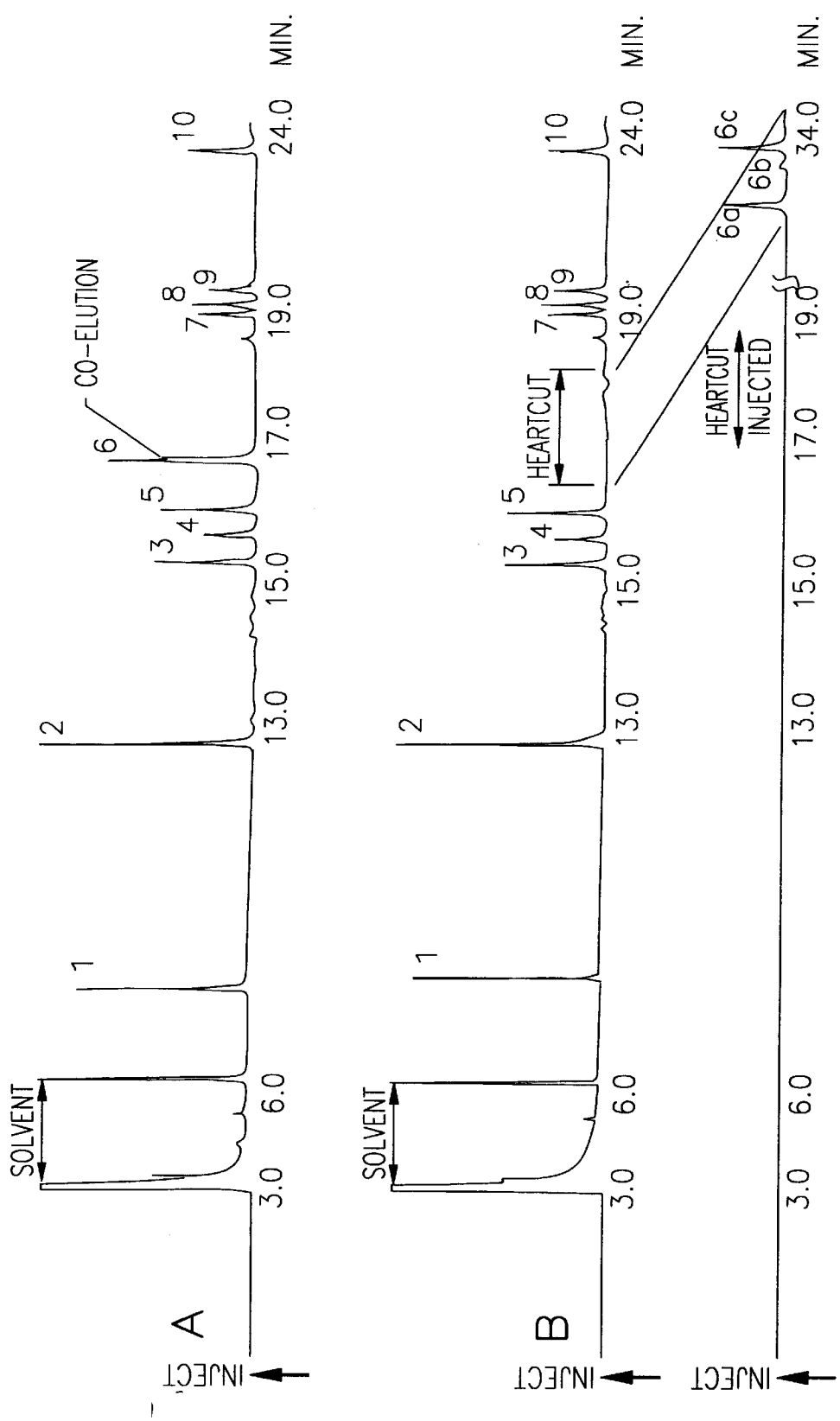
FIG. 1 is a graphic representation of the "heart-cutting" technique used in multidimensional gas chromatography known in the prior art.
Figure 2:
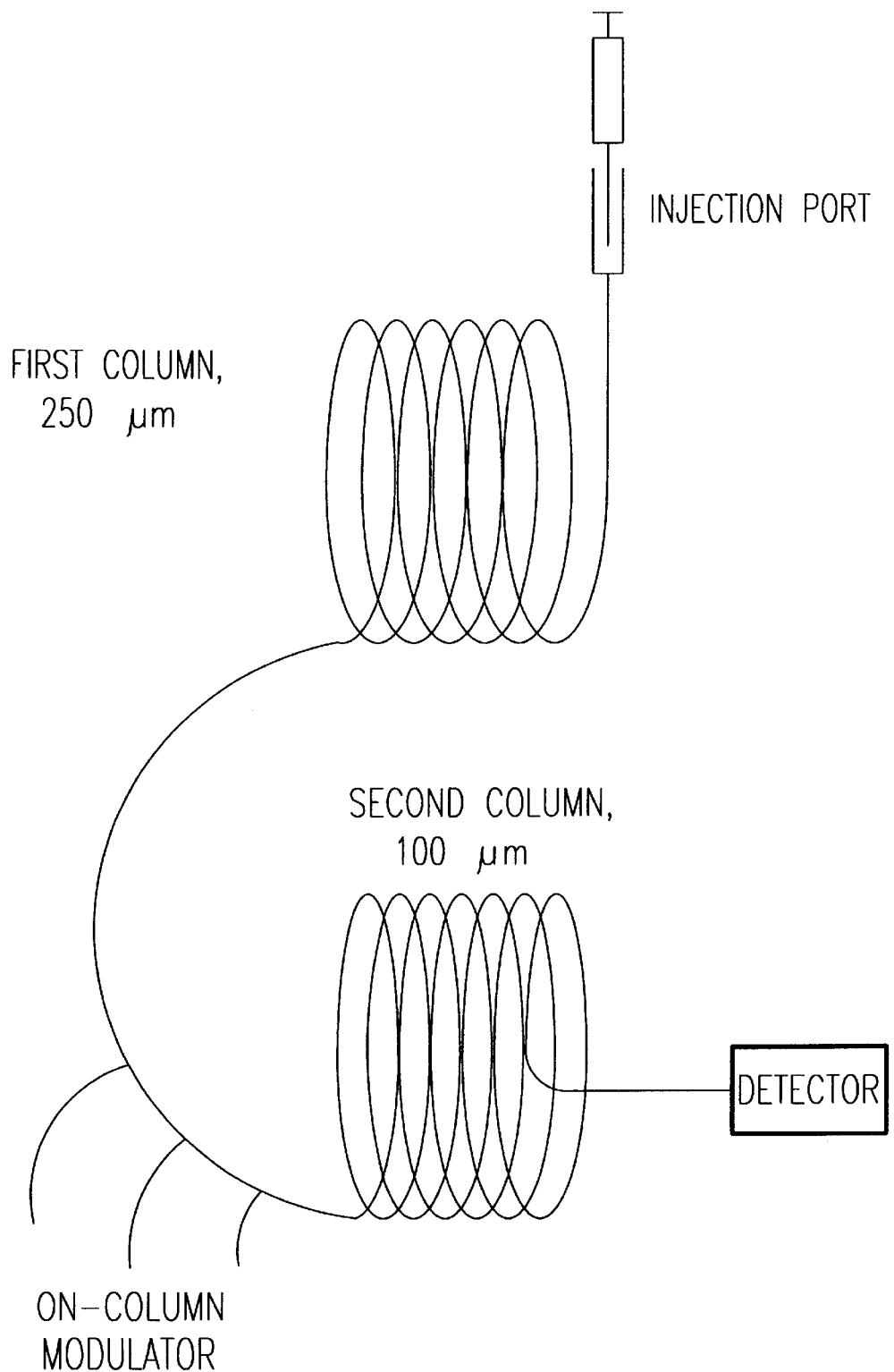
FIG. 2 is a schematic depiction of the technique of temperature modulation used in multidimensional gas chromatography known in the prior art.
Figure 3:
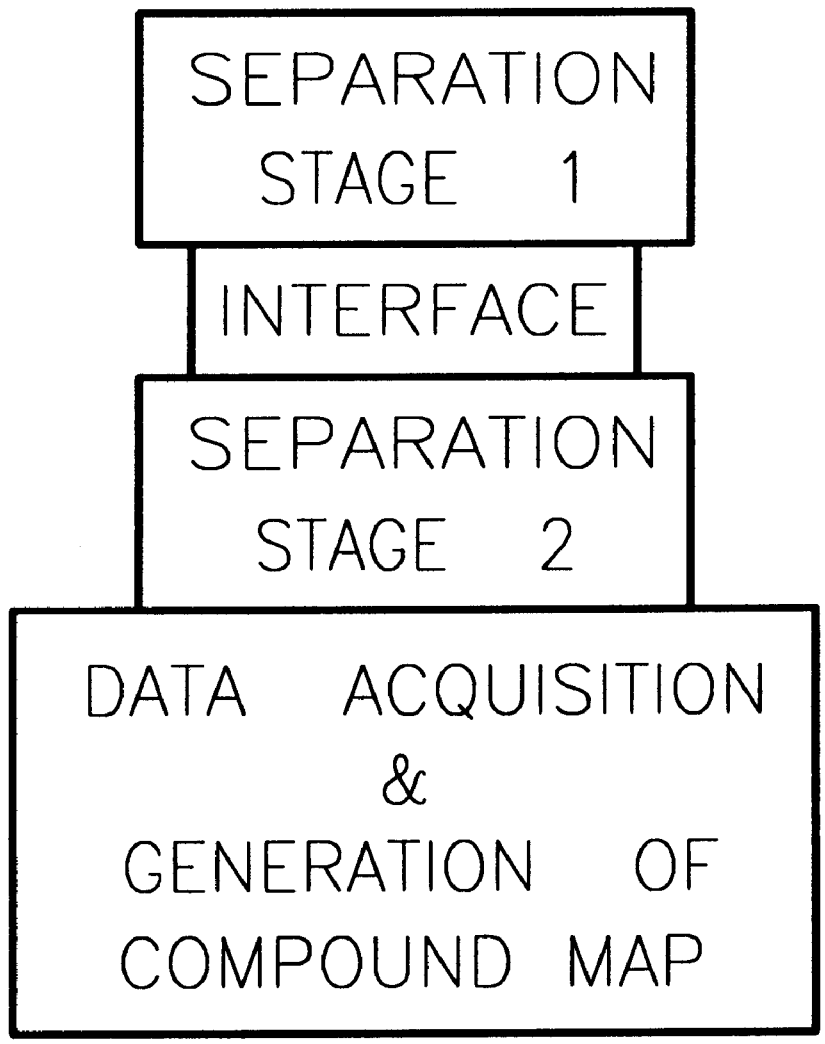
FIG. 3 is a block diagram of the time-coupled time-resolved chromatography (TCRC) method according to a preferred embodiment.
Figure 4:
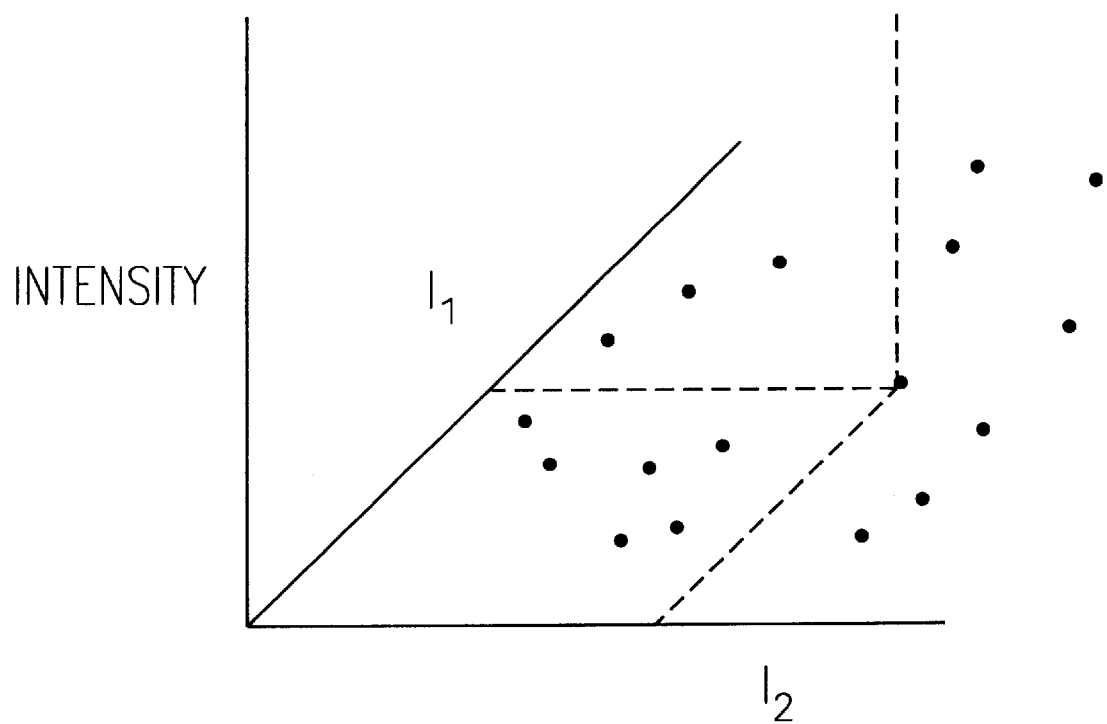
FIG. 4 is a three-dimensional graphic depiction of the coordinates for a compound.

The technique of time-coupled time-resolved chromatography (TCRC) is a multidimensional technique that operates in a different way than those described previously. In order to achieve multidimensional analysis, TCRC uses time coupling of two chromatographic columns physically coupled in series. As shown schematically in FIG. 3, the system uses a first separation stage which consists of a column maintained at low temperature (separation stage 1) in which some separation is achieved by scanning a narrow thermal zone alongside the column. This type of chromatography, called "chromathermography", has been studied previously and found to have a low separation power. The thermal zone, as it moves downwards, will carry compounds with the appropriate volatility down the column into an interface where the compounds are cryogenically trapped and then injected into a second separation stage. The second stage, which consists of a conventional gas chromatograph, then separates the compounds that have been "extracted" from the first column by the thermal zone. The entire process can be repeated at a higher temperature of the thermal zone and so on, until all the compounds present on the first column have been vaporized, transported into the analyzing system and separated. Thus, the second chromatograph resolves the components in time, and all the chromatograms that are acquired by repetitive and subsequent injection of the compounds carried by the thermal zone can be time-coupled. From the entire data set it is possible, as shown in FIG. 4, to plot a tridimensional map of the initial mixture in which each compound will be characterized by an intensity coordinate and two retention coordinates ($I_1, I_2$) corresponding to its retention properties in separation stages 1 and 2. If the detection system is a mass spectrometer, then the data will be represented in four dimensions, and this will increase selectivity.

The resulting map of the mixture is the result of the combined thermal-chromatographic process occurring in stage ($I_1$), and the chromatographic process occurring in stage 2 ($I_2$). If, for example, 400 compounds can be separated by the chromatograhic process in stage 2 (conventional gas chromatograph) and the thermal process in stage 1 has a temperature resolution of 10° C. for the range 50° C.–300° C., the total plane ($I_1, I_2$) will be able to accommodate 10,000 compounds [((300–50__/10)×400]. This technique, thus, offers a very high separation power, and this makes it of high analytical interest. As will be described further on there are other ways of operating an instrument based on TCRC technology.

Figure 5:
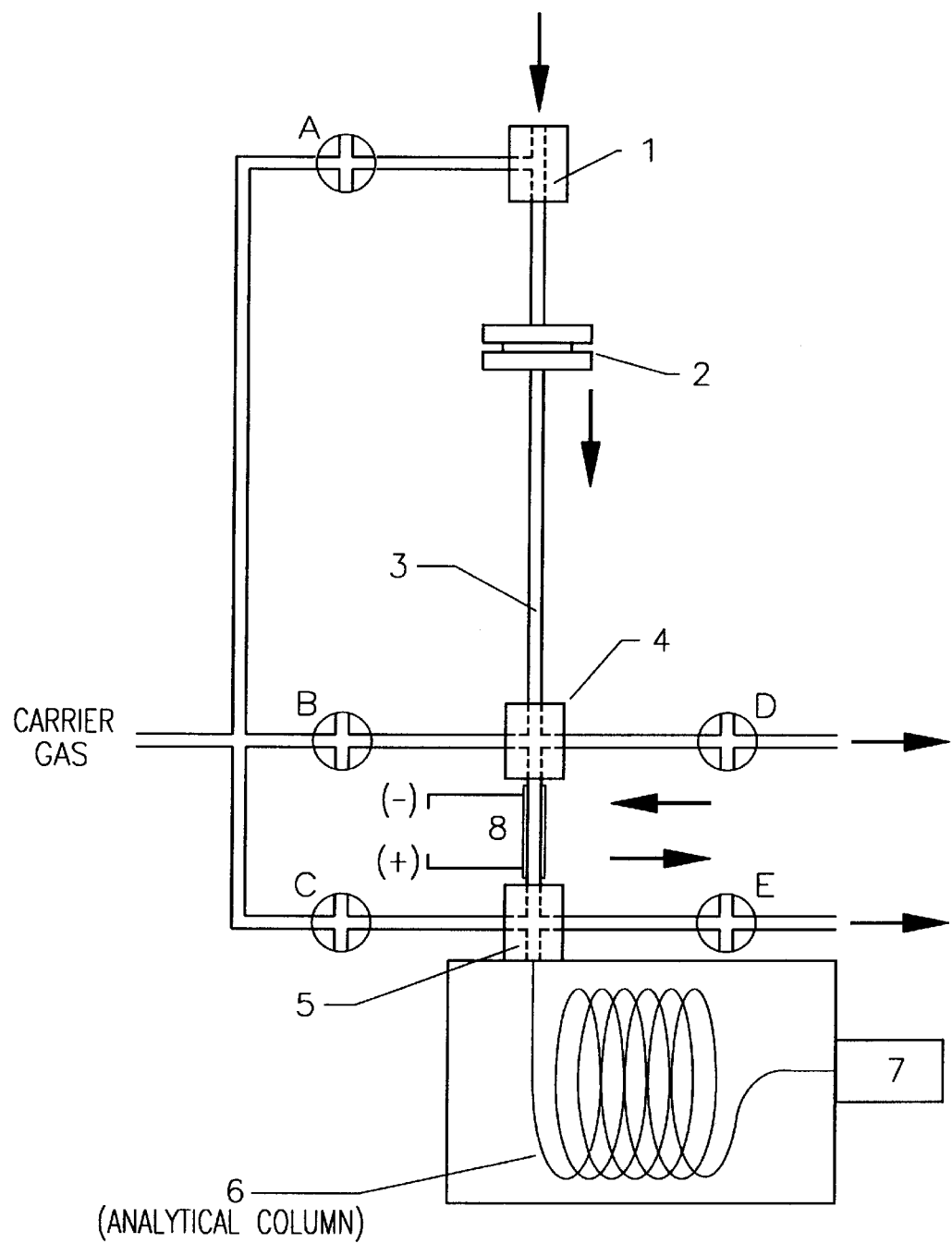
FIG. 5 is a schematic representation of the TCRC chromatograph.

A typical TCRC chromatograph is shown in FIG. 5. As can be seen from the figure, the first separation stage consists of an injector (1), a column operated at low temperature (ambient) (3) and a narrow thermal zone assembly (2) that can be scanned alongside the column. The rest of the stage includes a gas line that provides the carrier gas. The first stage is connected to the second stage through a first interface (4) and a cold trap (8). The second stage, which is a conventional chromatograph, consists of an interface (5) that is used as an injector, a megabore or a capillary analytical column (6) and a detector (7). Depicted are gas valves A, B, C, D and E.

Valves A and B, illustrated in FIG. 5, may be used separately as a high performance injector.

The injector is made of stainless steel. As can be seen in FIG. 5, it has a gas entrance on the left-hand side and holds the column at the bottom by a 'swage-lock' assembly. At the top of the injector, a septum is used in order to inject the sample onto the column with a syringe. The septum allows the system to be air-tight.

The cold column 3 in separation stage 1 is made of quartz or other similar materials. It is approximately 50 cm in length and varies from 0.5 mm to several mm in diameter. The inside diameter is 0.2 mm or more. The inside of the column is wall coated or packed with a chromatographic stationary phase distributed on particles of varying diameters. The stationary phase can vary in nature. The primary role of the column is to produce a primary separate of mixture components and freeze the separation outside the thermal zone assembly.

Figure 6:
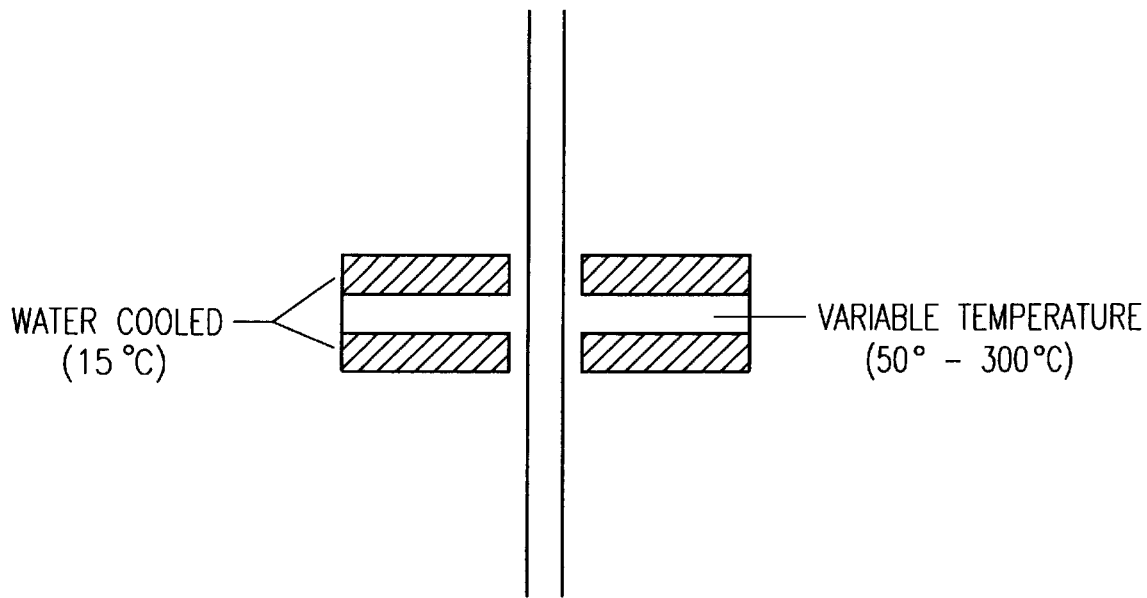
FIG. 6 is a schematic representation of the thermal zone assembly.

The scanning thermal zone assembly 3 comprises three elements, as shown in FIG. 6. The element in the center can vary in length from 1–6 mm and can be heated in between 50–300° C. On each side of the high temperature zone are placed two zones which are cooled by water or some other means (thermoelectrical device).

This assembly, which allows a square heat pulse to be obtained, is scanned alongside the column by means of a computer-controlled drive assembly. Although there is no limitation to the speed of the zone, it has to be slow enough so that proper heat transfer to the center of the column can occur efficiently. The temperature of the zone is variable from 50–300° C. and is regulated to 0.1° C. The lack of confinement of the high temperature zone by cold frontiers results in an inadequate heat profile, especially if the column is mounted vertically. The column can also be mounted horizontally.

This interface 4 allows the transfer of the compounds contained in the thermal zone to the cold trap. In other modes of operation (target compound analysis), the carrier gas exiting the column is allowed to be vented to atmosphere using valve D. The interface 4 is heated (~300° C.) and contains a spring-loaded device that reduces the effect of the cold zone at the bottom of the thermal assembly 3 on the transfer of the compounds trapped in the hot zone.

The cryogenic trapping zone 8 is used to condense volatile compounds eluting from the first column during the scan of the thermal assembly 3. Once the scan(s) is terminated, the content of the trap can be injected in the second stage by flash-heading heating the trap. There are several ways to cool or flash-heat the trap. The second trap can be flushed at any time by inputting gas through valve B and venting the gas through valve E.

Interface 5 is used in order to transfer the compounds frozen in the trap to the second stage of separation after the flash-heating of the trap. It is used as an injector for the conventional chromatograph used in the analysis stage. It is usually heated at ≈300° C. and can be used to vent the trap by opening valve E. It can also be used to input the carrier gas in the second column through valve C during analysis in the second stage. In this fashion, the second stage can be operated independently from the first, or scanning in the first section can be conducted concurrently to analysis in the second stage.

The analyzer column 6 resides inside a conventional gas chromatograph which is operated in an isothermal or temperature programmed mode. The column can be a capillary or megabore type column. Its role is to separate the components that have been transported by the scan of the thermal zone and trapped. The temperature cycle of the analyzer column can be matched with that of the thermal zone assembly. The nature of the stationary phase on this chromatographic column can be different or similar to that used in the first column.

The detection system 7 used in TCRC can be any detector that is presently used in gas chromatography or a mass spectrometer. When a mass spectrometer is used (TCRC/MS), the selectivity of the system is increased tremendously because the technique operates in four dimensions instead of three. Other advantages of the mass spectrometer such as its selected ion monitoring mode, can also be used.

The detection system is interfaced to a data acquisition and treatment station that is also used to generate the output of the analysis showing the components in the mixture. The output map has to be calculated in a special way for the data to be reproducible, and this will be discussed in the operation modes below.

The three basic modes of operation are: i) emulation of a gas chromatography ii) target compound analysis and iii) full mixture mapping.

When the system emulates a conventional gas chromatograph, the TCRC instrument is operated in the following way. The mixture to be analyzed is injected in stage 1 and the thermal zone is scanned down the column once or several times, depending on the quantity of compounds present at its maximum temperature ($\approx$300–350° C.). In this way, all the volatile components in the mixture are transported by the thermal zone and they are simultaneously injected in the second stage. The analyzer column is, thus, temperature programmed from 50° C. to $\approx$350° C. and produces a single chromatogram of the mixture in which all the components are present.

The chromatogram generated in this operating mode is similar to what would be obtained if the mixture was analyzed on a conventional chromatogram, as shown in FIG. 7, where the top chromatogram was obtained on a conventional chromatograph and the bottom, on the TCRC instrument emulating a conventional chromatograph. However, the performance, in terms of sensitivity and resolution, can be better (two- to fourfold) on the TCRC instrument because of the band compression phenomenon occurring in the first stage.

The second mode of operation of the TCRC instrument is the mode for target compound analysis (TCA). This mode allows the rapid and selective analysis of predetermined compounds in a mixture. In this mode, once the temperature for extracting the compound of interest in the separation stage 1 has been determined, the thermal assembly is scanned just below that temperature. With valve D opened to the atmosphere, the scan, containing all the compounds more volatile than the compound of interest, is vented. The next scan is conducted at the appropriate temperature for the compound of interest to be transported by the thermal zone assembly and transmitted to the second stage which will conduct further separation of the compounds eluted in this scan. Since most of the more volatile compounds have been eliminated by the first scan, and the less volatile will have stayed behind at the temperature of the second scan, it is possible to rapidly analyze the desired compound with high sensitivity and selectivity. If other compounds need to be analyzed in the same mixture, then the process can be continued by successively discarding the fractions at a temperature lower than that of the desired compounds and scanning the thermal assembly at the appropriate temperature for each of the compounds of interest. This scan mode is unique to TCRC and is shown in FIG. 8, where the top chromatogram was obtained on a conventional gas chromatograph, and the component of interest ($C_{15}$) was selectively analyzed from the mixture by the TCRC instrument in its target compound mode. This procedure will enable the analyst to save time while maintaining high sensitivity and selectivity in the analysis. The latter mode has many applications in the field of quality control or environmental control.

The third mode, which is the full mapping mode, is used to systematically analyze all the components of a mixture. In this mode, the thermal assembly is scanned alongside the first column starting at a low temperature (50° C.) and its content of volatile components transferred to the second stage of analysis. Then, the hot zone is increased in temperature ($\approx$+10° C.) and re-scanned with transfer of its content and analysis in the second zone. This process is repetitively done until the total temperature range of the thermal assembly has been covered ($\approx$50–350° C.). At each temperature that the thermal assembly is scanned alongside the first column, a chromatogram is obtained from stage 2 and these chromatograms are stored in the memory of the data acquisition system. Each of these chromatograms represents the separation of components that have been extracted from the mixture at a given temperature and transported by thermal assembly. It is therefore possible to map the entire mixture by plotting each of the time-resolved chromatograms in a time-coupled fashion, as shown in FIG. 9.

In this fashion, all the chromatograms obtained in the second stage will be from left to right on the retention time axis. By plotting each chromatogram at the temperature it was obtained from the initial temperature ($T_i$) to the final temperature ($T_f$), all chromatograms are now linked together (time-coupled). The third axis is the intensity axis where the intensities of each peak (not shown) in the chromatograms are displayed. The map shown in FIG. 9, thus, represents the new data matrix provided by the technique in the full map scan mode.

Figure 9:
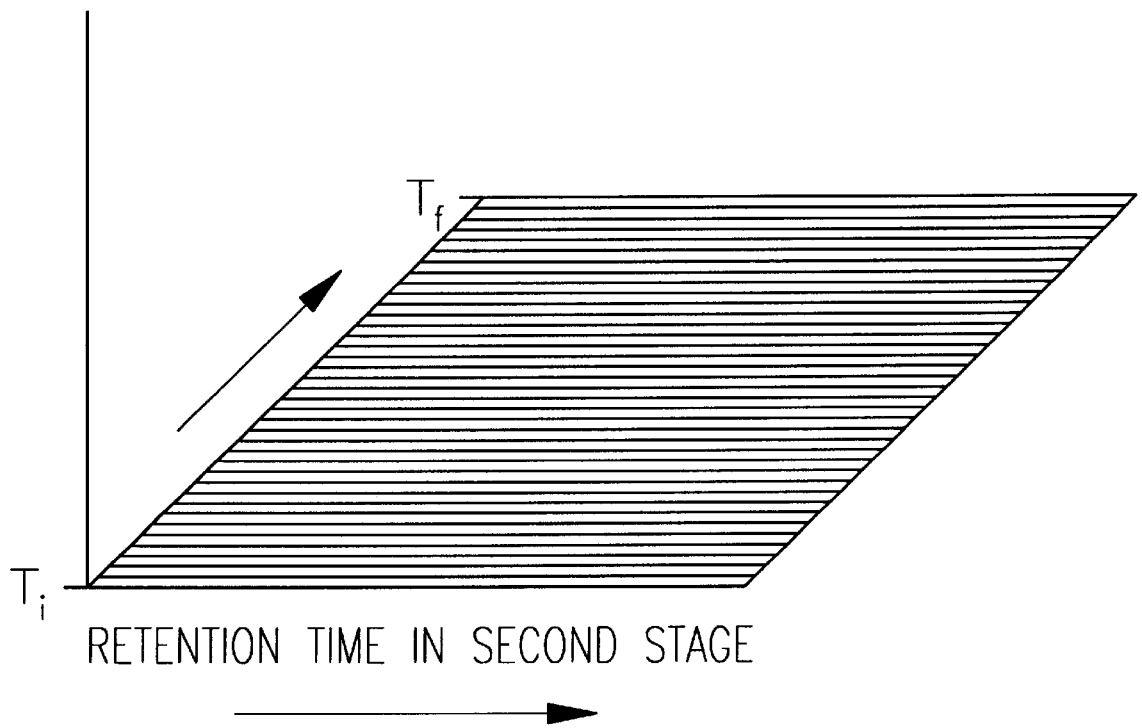
FIG. 9 is a graphic representation of the TCRC device in the full mapping mode.

Because of variation in several experimental parameters, however, the map shown in FIG. 9 is of limited usefulness because it is difficult to reproduce the raw data. This is due to the fact that the temperature of the thermal assembly is jumped and not varied continuously, and that the same compound may elute out of the first system in two scans rather than one (two temperatures). A compound which is just not sufficiently volatile to be completely eluted by the hot zone at a given temperature will partly elute at one temperature, and its elution will be completed in the following scan at a higher temperature. This compound will produce two peaks in the data set, which is not desirable. Furthermore, the temperature at which a compound elutes is not constant but varies with column parameters and the speed at which the thermal assembly is scanned. Since in the full map mode, very complex mixtures have to be analyzed, these uncertainties in the raw data can create serious difficulties.

It is possible to eliminate the difficulties mentioned above by using reference compounds for the system and constructing the map by calculations. Actually, if instead of using raw retention times one uses indices that convert retention times relative to those of the reference compounds, and instead of using extraction temperatures, one uses indices converting extraction temperatures relative to those of a reference compound, then the calculated map of the mixture can become independent of most experimental parameters and reproducible. In order to clarify this conversion procedure and explain how a usable map can be obtained, we will describe the conversion procedure for both axes.

The characterization of the compounds eluting from the first stage of the system is most difficult and critical since the extraction temperature can vary with other parameters such as speed of the thermal assembly, and a single compound can elute in two different scans (different temperatures) because its thermal properties do not match the jumps used in the extraction temperatures. Since the temperature of the scans is steadily increased by a constant and arbitrary value, there will always be a compound that will have a true elution (extraction) temperature in between the values of two scans. For example, if the true elution temperature of a compound is 58° C., the scan at 50° C. will not be sufficiently hot to totally elute the compound, which will require the next scan at a higher temperature of 60° C. to elute in totality. Therefore, the elution temperature in the first stage of the TCRC instrument will be calculated as the centroid ($T_e$) of the eluting temperatures, as shown in the equation below [1]. In the equation, $I_i$ refers to the intensities of the peak eluting at temperature $T_i$. Thus, if a peak elutes at 20% at a temperature of 50° C. and 80% at a temperature of 60° C., its centroid temperature will be equivalent to 58° C. This way of calculating the elution temperature is, therefore, appropriate to the technique and will compensate for the fact that the scanning temperature is jumped instead of being varied continuously.

$$T_e = \frac{\sum I_i \times T_i}{\sum I_i} \qquad [1]$$

The elution temperature can be converted to the elution time ($t_e$) with the aid of equation [2]. In this equation, $I_i$ refers to the intensities of the peak eluting in scan $S_i$ and t is the time required for one scan of the thermal assembly. Thus, if a compound elutes as previously at 20% in the first scan, and at 80% in the second scan, and the scan time is 1 minute, its apparent elution time will be 1.8 minutes.

$$t_e = \frac{\sum I_i \times t \times S_i}{\sum I_i} \qquad [2]$$

The second difficulty that occurs is the variation of the elution temperature in the first stage with experimental conditions. This problem can be solved by using reference compounds to compensate for this effect. Because the difficulty mainly arises from variations in the eluting temperature with scan speed the variations will also be felt by a reference compound. Since the phenomenon occurring in the first stage can be compared to a distillation, hydrocarbons can be used as reference compounds. If the temperatures of elution of a series of hydrocarbons (n-alkanes ranging from $C_5$–$C_{40}$) are measured in the system, it will always be possible to brake a compound eluting at temperature $T_e$ by two hydrocarbons with elution temperatures above ($T_{H+1}$) and below ($T_H$) the compound. In terms of elution times, the corresponding values will be $t_e$, $t_{H+1}$ and $t_H$. It is thus possible to calculate an elution index for the compound ($I_i$) which will quantify its elution properties relative to the hydrocarbons, and the index is obtained with equation [3]. In the equation, n represents the number of carbon atoms of the lower hydrocarbon, while $t_i$, $t_{H+1}$ and $t_H$ represent the calculated elution times for the compound and the two hydrocarbons respectively. The index can also be calculated using elution temperatures.

$$I_{1i} = 100n + 100 \left[ \frac{\log(t_i / t_H)}{\log(t_{H+1} / t_H)} \right] \qquad [3]$$

The situation for the calculation of an index in the second stage is similar to the first stage. However, in this case, the situation is less complex due to the fact that in the second stage, the analysis is essentially that of a normal chromatogram. In this case, the index will be calculated from the corrected retention times of the compounds.

$$t_{Ri}^* = t_{Ri} - t_m \qquad [4]$$

The corrected retention time ($t_{Ri}^*$) for a compound is given by equation [4] where $t_{Ri}$ and $t_m$ refer to the measured retention time and deadtime in the system. By using these corrected retention times it is possible as before to calculate an index for the second stage ($I_{2i}$) based on the retention times of hydrocarbons (n-alkanes), and this can be done with the use of equation [5] where $t_{Ri}^*$, $t_H^*$ and $t_{H+1}^*$, represent the corrected retention times of the compounds and the hydrocarbons below and above it respectively. This second index, like the first, can be used to characterize the retention properties of the analytes in the second system and allow, with the first index, the construction of the map of the mixture.

$$I_{2i} = 100n + 100 \left[ \frac{\log(t_{Ri}^* / t_H^*)}{\log(t_{H+1}^* / t_H^*)} \right] \qquad [5]$$

Figure 10:
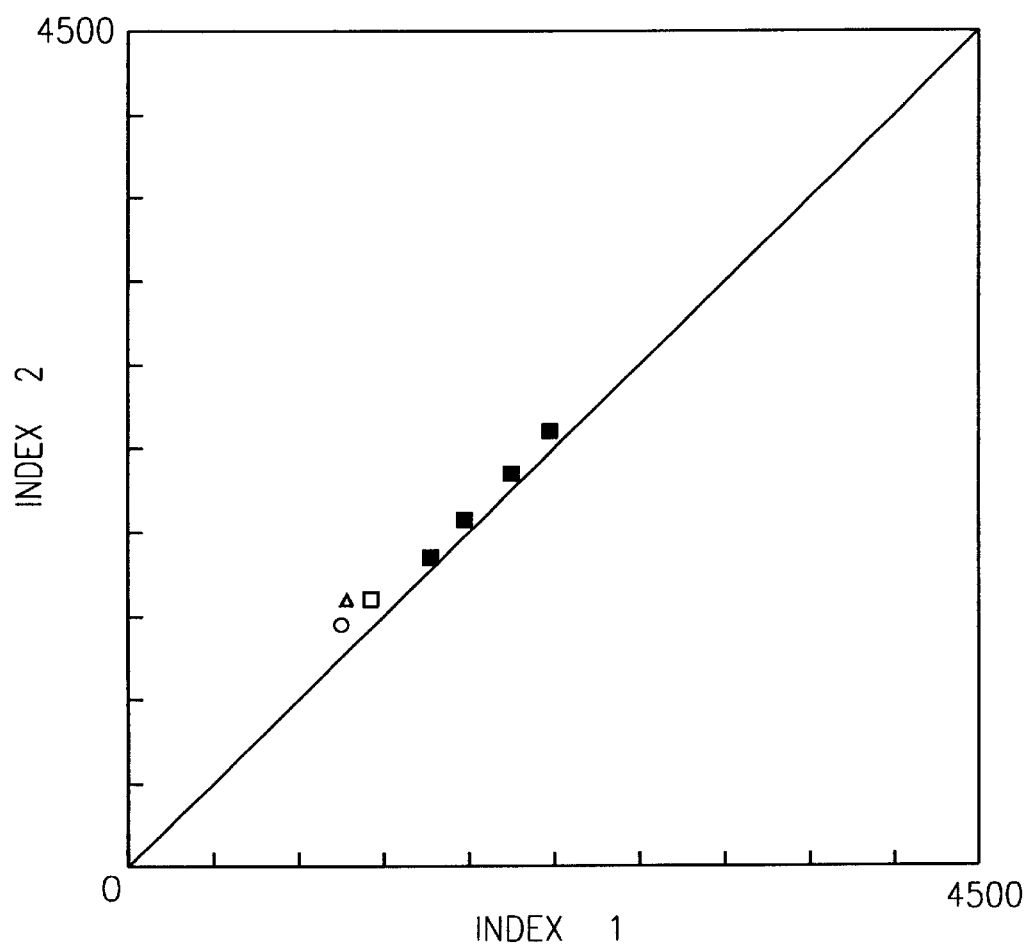
FIG. 10 is a graphic representation of the TCRC of a reconstructed map in the full mapping mode.

An example of the results obtained in the full mapping mode is presented in FIG. 10, where several compounds have been injected and the resulting TCRC map calculated in the fashion specified. The map is constructed by giving an index of 100 units per carbon atom number for the alkanes so that the range in indices $I_1$ and $I_2$ is from 0 to 4500 representing alkanes up to 45 carbon atoms which are volatile within the working temperature range. Because of the way the reference system is chosen, the median line in the map represents a line along which all the n-alkanes are aligned. The other compounds appear as points in the plane each having two coordinates ($I_1$,$I_2$). The intensities of the peaks are ln the third dimension which is not shown on the map of FIG. 10. One of the ways to represent these intensities is to project the sum of all the intensities found in the $I_1$ axis on the $I_2$ axis, and project the sum of all the intensities found in the $I_2$ axis on the $I_1$ axis, thus, generating two visual chromatograms, one on the $I_1$ axis and one on the $I_2$ axis, on which the intensities would appear as normalized values. This representation would allow to see where each of the peaks in the map stands relative to the mixture (plane) but also relative to the bands eluting in the first or second separation stage.

An analytical feature of this mapping system which is unique to this technique is its ability to give an overall view of the components of the mixture, which can be used to follow a situation or indicate the presence of homologous compounds without the necessity of identifying all the components present in the mixture.

Because of the reference system used, homologous compounds (those belonging to a chemical family) will appear as patterns in the map. This can be seen from FIG. 10, where the four black squares appear as a line in the data plane. Those four compounds are esters of fatty acids ranging from $C_{19}$ to $C_{23}$. The other three compounds present in the map are not related to the esters, and therefore appear in a random fashion. Hence, because of this reconstructed map of the mixture, not only are the data reproducible in this format, but additional and unique information can be obtained from the data.

The three operation modes that have been described for the TCRC technique have many analytical applications in chemical analysis and each of the modes, except for the GC emulation mode, provides new methods of analysis that allow unique data to be obtained. Most of the obvious applications in the areas of chemical analysis are known to us, and it can be predicted that TCRC or TCRC/MS has an enormous potential as a new analytical technique. The unique assembled techniques of the present invention yield results that cannot be obtained by other techniques, and represent an entirely new way of looking at a sample.

The principle that is used in the mobile zone thermal extractor is based on the difference in volatility between various components in a mixture and also on varying affinities of these components for a given adsorbent. If a mixture containing several relatively involatile compounds is deposited in a column containing a stationary phase or packing (adsorbant) and the column is maintained at ambient temperature, the compounds will remain mostly in the stationary phase. The partitioning of each compound between the gas phase and the stationary phase will be given by equations [6] and [6] where $C_g$ and $C_s$ represent the concentration in the gas phase and the stationary phase and $C_0$ is the total concentration.

$$C_g = C_0(1/1+k') \quad [6]$$

$$C_s = C_0(k'/1+k') \quad [7]$$

As can be seen from the equations if the capacity ratio k'(affinity for the stationary phase) is high which is the case at low temperature then $C_g$ will be small and $C_s$ will be large demonstrating that most of the compounds will be in the stationary phase where they are not transported by the carrier gas passing in the column with a velocity $v_C$. However, if a concentric narrow high temperature zone bordered by two cold zones producing a square heat wave is passed alongside the column the high temperature will cause a significant decrease in k' and the compounds will tend to pass into the gas phase as shown by equation [6] and [7] since $C_g$ will increase and $C_S$ will decrease.

Thus, the more volatile compounds will be carried through the column by the carrier gas if its velocity $v_C$ is greater than that of the thermal assembly $v_F$.

Assuming that the capacity ratio k' for compound 1 is zero at the temperature of the zone than $C_g$ will be equal to $C_0$ for this compound and it will be entirely transported by the gas pocket contained in the thermal zone assembly and it will elute from the column. Compound 2 which is less volatile will migrate partly and compound 3 which is not volatile will essentially not migrate and stay at the beginning of the column. Hence, it has been possible in the given example to isolate or thermally extract compound 1 from the mixture.

In a similar way, assuming that compound 2 was the compound of interest, it would be possible to make a second scan of the thermal zone assembly at a slightly higher temperature and to elute compound 2 while compound 3 which is much less volatile will migrate somewhat but will not elute. In the latter case the first run would have been vented in order to eliminate compound 1 and the second run would have used a trapping device in order to collect compound 2. Therefore, whatever the relative volatility of a compound in a mixture may be, it will always be possible by the use of the appropriate temperature and scan sequence to isolate it (with varying purity) from the other components having different volatility or capacity ratio (k'). If the compound to be extracted is known, it is possible to use it as a standard to calibrate the operating conditions for its isolation. If the compound is not known, the operating conditions can be obtained from knowledge of its chromatographic behavior using a conventional chromatograph.

A typical assembly for the moving zone thermal extractor is depicted in FIG. 5. The carrier gas (Helium) is introduced in the system by opening valve A which is connected to the injector. The sample is introduced in the injector using a syringe through a septum or another injection device and the mixture is deposited on the packed column. The column can have different diameters or lengths depending on the application and the amount of compound to be isolated.

Typically the length would vary between 50 and 200 cm and the diameter from 1 mm to several centimeters. The thermal zone temperature which includes a hot zone of varying temperature ($\approx 20$–$400°$ C.) between two cold zones (water cooled or by forced convection or thermoelectrically) is set to a value below the elution temperature of the compound of interest and is passed over the mixture and scanned alongside the column. In order to eliminate the more volatile materials, valve B is opened and valve C is closed. This configuration will force the gas and the compounds carried by the thermal zone out through B. One or more scans can be performed in this configuration depending on the application and the temperature used. Then, the temperature of the zone is set to the elution temperature of the compound of interest and the zone is scanned closing valve B and opening valve C. This will force the compound in a trapping device where it can be collected using several means depending on the particular experiment being conducted.

For example, one can use a cold trap in order to collect the compound of interest. Conditions in the transfer interface which is used to vent or collect the sample eluted by the thermal zone can vary. For each type of application the temperature of the thermal zone, the flow of the carrier gas, the velocity of the mobile zone, the nature of the stationary phase and the number of scans performed are all variables that have to be optimized.

Figure 15:
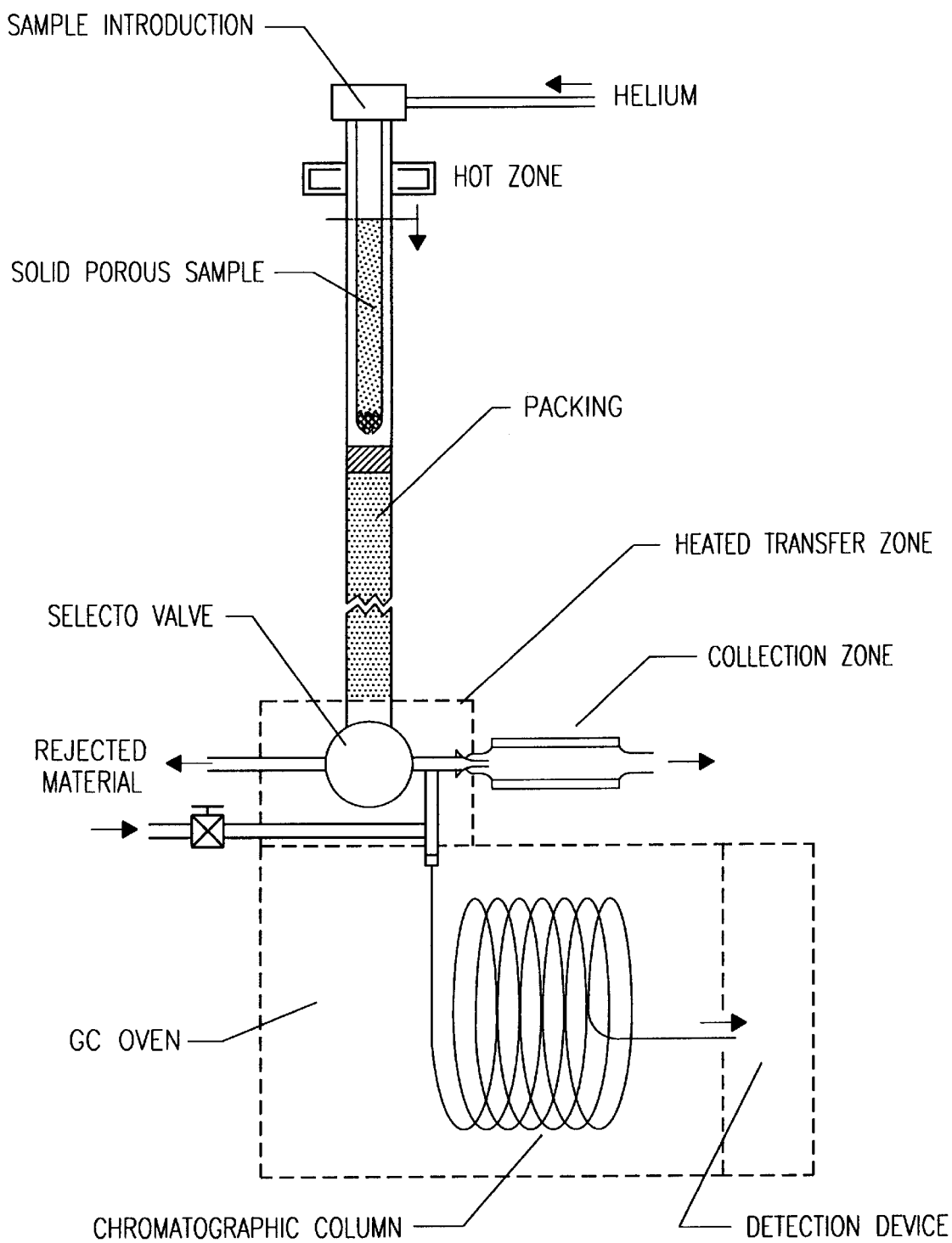
FIG. 15 is a schematic view of thermal extraction device according to the invention.
Figure 16:
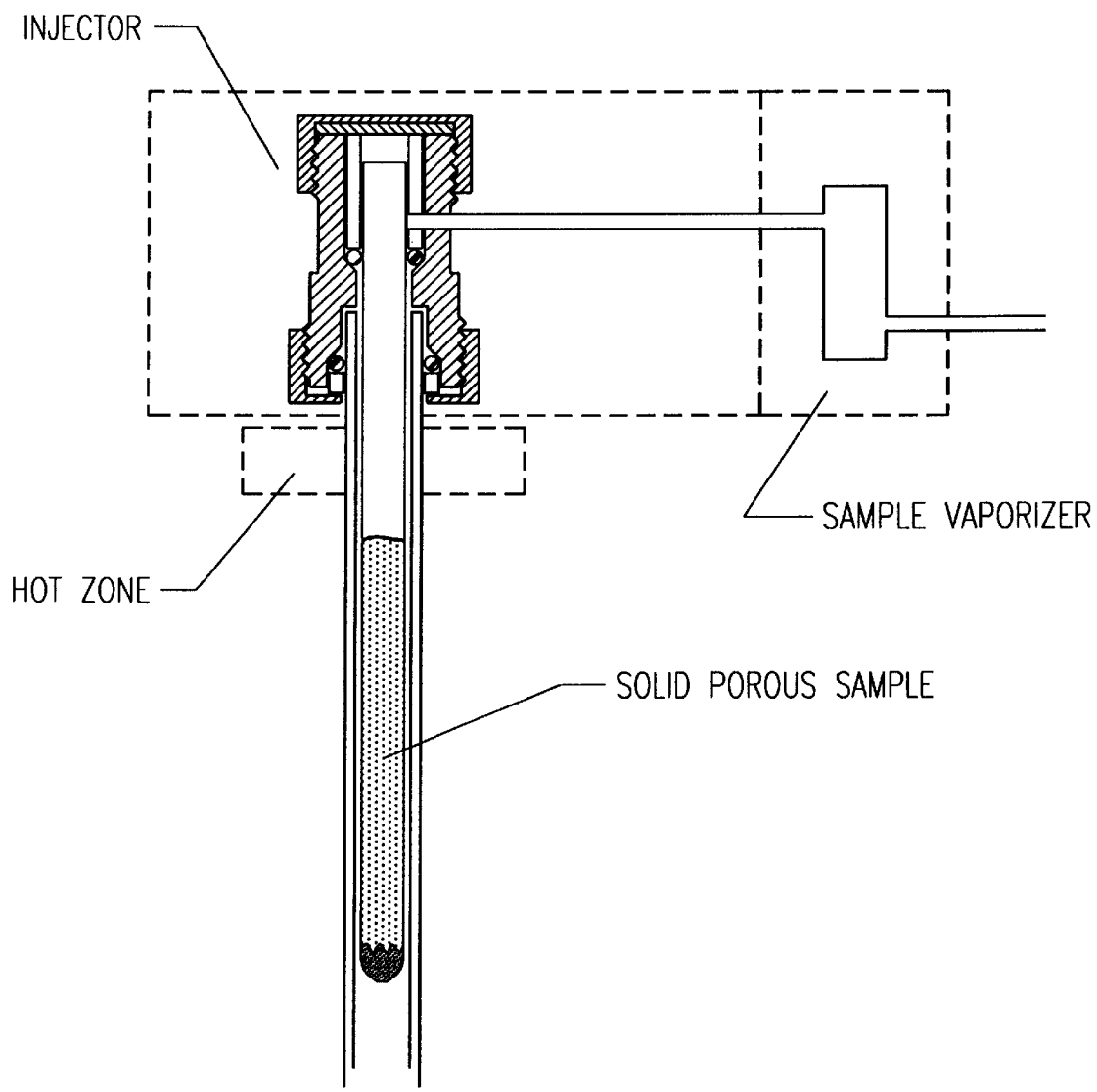
FIG. 16 is a more detailed view of the injector illustrated in FIG. 15.

A more detailed diagram which explains the general operation of a thermal extractor is shown in FIG. 15. With this arrangement, a solid sample (or a liquid on a substrate) is placed in a cartridge and submitted to the thermal extraction process and purification through the column. By selecting the valve position, compounds may either be discarded or sent to a collection zone. Splitting the gas flow before this zone allows the gas chromatographic analysis of the collected fraction.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

I claim:

1. An apparatus for analyzing complex mixtures of organic chemical compounds comprising the serial combination of a first chromatography stage and a second separation stage, said apparatus comprising, in sequence: a first column maintained at low ambient temperature, wherein separation is achieved by scanning a thermal zone assembly alongside said first column; an interface; and a cryogenic trapping zone connecting said first separation stage to said second separation stage, wherein said second separation stage comprises an analytical column and a detector.

2. The apparatus in accordance with claim 1, wherein said analytical column is a capillary column or a megabore column.

3. The apparatus in accordance with claim 1, wherein said scanning of said thermal zone assembly is repeated at least once at a higher temperature of the thermal zone assembly until at least one compound present in said first column has been vaporized, trapped in said cryogenic trapping zone, transported into said second separation stage and analyzed.

4. An apparatus for analyzing complex mixtures of organic chemicals comprising a chromathermography device and a gas chromatograph, arranged in serial combination, said chromathermography device and said gas chromatograph having separately controllable carrier gas controls to provide for different gas flow rates in said device and said chromatograph.

5. An apparatus for analyzing complex mixtures of organic chemicals in accordance with claim 4, wherein said chromathermography device and gas chromatograph are releaseably connectable.

6. An apparatus in accordance with claim 4, further comprising an interface and a cryogenic trapping zone placed between said chromathermography device and said gas chromatograph.

7. An apparatus in accordance with claim 4, wherein said chromathermography device comprises an injector, a first column and a thermal zone assembly arranged alongside said column.

8. An apparatus in accordance with claim 4, wherein said gas chromatograph comprises an injector, an analyzer column and a detector.

* * * * *

UNITED STATES PATENT AND TRADEMARK OFFICE
CERTIFICATE OF CORRECTION

PATENT NO. : 6,311,544 B1                           Page 1 of 1
DATED      : November 6, 2001
INVENTOR(S) : Michel Bertrand It is certified that error appears in the above-identified patent and that said Letters Patent is hereby corrected as shown below:

Title page,
Item [62], Related U.S. Application Data, should read:
-- [621 Continuation of application Ser. No. 09/181,860, filed on October 29, 1998, now U.S. Patent No. 6,131,440, which is a divisional of application Ser. No. 08/730,395, filed on October 15,1996, now U.S. Patent No. 5,929,321 --

Column 1,
Lines 6-10, should read:
-- This application is a continuation of application Ser. No. 09/181,860, filed on October 29, 1998, now U.S. Patent No. 6,131,440, which is a divisional of application Ser. No. 08/730,395, filed on October 15, 1996, now U.S. Patent No. 5,929,321. --

Signed and Sealed this

Tenth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,311,544 B1
DATED : November 6, 2001
INVENTOR(S) : Michel Bertrand It is certified that error appears in the above-identified patent and that said Letters Patent is hereby corrected as shown below:

Title page,
Item [62], Related U.S. Application Data, should read:
-- [62] Divisional of application Ser. No. 09/181,860, filed on October 29, 1998, now U.S. Patent No. 6,131,440, which is a divisional of application Ser. No. 08/730,395, filed on October 15,1996, now U.S. Patent No. 5,929,321 --

Column 1,
Lines 6-10, should read:
-- This application is a divisional of application Ser. No. 09/181,860, filed on October 29, 1998, now U.S. Patent No. 6,131,440, which is a divisional of application Ser. No. 08/730,395, filed on October 15, 1996, now U.S. Patent No. 5,929,321. --

Signed and Sealed this

Sixth Day of July, 2004

JON W. DUDAS
*Acting Director of the United States Patent and Trademark Office*